United States Patent [19]

Galleguillos et al.

[11] Patent Number: 5,534,245

[45] Date of Patent: Jul. 9, 1996

[54] ANTIPERSPIRANT DEODORANT COMPOSITIONS

[75] Inventors: Ramiro Galleguillos, Glendale Heights; Billie L. Radd, Naperville; Anjana K. Jadav, Chicago, all of Ill.

[73] Assignee: Helene Curtis, Inc., Chicago, Ill.

[21] Appl. No.: 373,111

[22] Filed: Jan. 17, 1995

Related U.S. Application Data

[63] Continuation-in-part of Ser. No. 199,492, Feb. 22, 1994.

[51] Int. Cl.$^6$ .............................. A61K 7/34; A61K 7/38
[52] U.S. Cl. ................................... 424/66; 424/68
[58] Field of Search ................... 424/65, 66, 68

[56] References Cited

U.S. PATENT DOCUMENTS

| | | | |
|---|---|---|---|
| 2,607,658 | 8/1952 | Govett et al. | 23/14 |
| 2,645,616 | 7/1953 | Govett et al. | 252/317 |
| 2,876,163 | 3/1959 | Garizio et al. | 167/90 |
| 3,255,082 | 6/1966 | Barton | 167/90 |
| 3,740,421 | 6/1973 | Schmolka | 424/65 |
| 3,822,238 | 7/1974 | Blair et al. | 260/75 NK |
| 3,975,350 | 8/1976 | Hudgin et al. | 260/30.4 N |
| 4,156,066 | 5/1979 | Gould | 528/73 |
| 4,156,067 | 5/1979 | Gould | 528/73 |
| 4,255,550 | 3/1981 | Gould | 528/44 |
| 4,268,499 | 5/1981 | Keil | 424/68 |
| 4,278,655 | 7/1981 | Elmi | 424/47 |
| 4,350,605 | 9/1982 | Hughett | 252/305 |
| 4,359,558 | 11/1982 | Gould et al. | 525/454 |
| 4,383,988 | 5/1983 | Teng et al. | 424/68 |
| 4,451,635 | 5/1984 | Gould et al. | 528/71 |
| 4,454,309 | 6/1984 | Gould et al. | 525/454 |
| 4,673,570 | 6/1987 | Soldati | 424/66 |
| 4,725,430 | 2/1988 | Schamper et al. | 424/66 |
| 4,743,673 | 5/1988 | Johnston et al. | 528/60 |
| 4,822,602 | 4/1989 | Sabatelli | 424/65 |
| 4,904,466 | 2/1990 | Carson | 424/76.3 |
| 5,000,955 | 3/1991 | Gould et al. | 424/409 |

FOREIGN PATENT DOCUMENTS

| | | |
|---|---|---|
| 0448278 | 9/1991 | European Pat. Off. . |
| 0450597 | 10/1991 | European Pat. Off. . |
| 0512770 | 11/1992 | European Pat. Off. . |
| 0550960 | 7/1993 | European Pat. Off. . |
| WO91/15191 | 10/1991 | WIPO . |
| WO92/05767 | 4/1992 | WIPO . |
| WO92/19222 | 11/1992 | WIPO . |

OTHER PUBLICATIONS

C. Fox, "Antiperspriants & Deodorants Review and Update", *Cosmetics & Toiletries*, 100, pp. 27–41 (1985).

Anon., "Deodorant & Antiperspirant Formula", *Cosmemtics & Toiletries*, 100, pp. 65–75 (1985).

P. R. Howard et al. "Chapter 12—Systems Approach for Rheology Control", in *Polymers as Rheology Modifiers*, pp. 207–221 (1991).

R. L. Goldemberg, et al. "Silicones in Clear Formulations", *D&CI*, pp. 34–44 Feb. 1986.

Kirk–Othmer, *Encyclopedia of Chemical Technology*, Fourth Edition, Vol. 5, John Wiley and Sons, New York, NY, pp. 548–549 (1993).

*Remington's Pharmaceutical Sciences, Eighteenth Edition*, A. Gennaro et al., ed., Philadelphia College of Pharmacy and Science, Mack Publishing Co., Easton, PA, p. 761 (1990).

*Primary Examiner*—C. Warren Ivy
*Assistant Examiner*—Evelyn Huang
*Attorney, Agent, or Firm*—Marshall, O'Toole, Gerstein, Murray & Borun

[57] ABSTRACT

Roll-on or gel antiperspirant compositions comprising an antiperspirant compound, a hydrophilic polymer, a carrier, and, optionally, a softening agent, are disclosed.

27 Claims, No Drawings

ANTIPERSPIRANT DEODORANT COMPOSITIONS

This application is a continuation-in-part application of pending U.S. Ser. No. 08/199,492, filed on Feb. 22, 1994.

FIELD OF THE INVENTION

The present invention is directed to antiperspirant compositions comprising an antiperspirant compound, like an astringent salt; a hydrophilic polymer, like a hydrophilic polyurethane having a molecular weight of at least about 10,000; a carrier; and optionally, a softening agent, like a nonionic surfactant. The antiperspirant compositions are viscous compositions that typically are transparent, phase stable and essentially nonwhitening and nonstaining to skin and clothing after topical application; effectively deliver the antiperspirant compound to the skin; and exhibit excellent sensory properties. The present invention also is directed to methods of using the antiperspirant compositions.

BACKGROUND OF THE INVENTION

Antiperspirant compositions are well-known in the cosmetic art. An ideal antiperspirant composition is stable for the life of the composition, effectively delivers the antiperspirant compound to the skin, does not leave a visually-observable white residue on the skin or clothing, and is esthetically pleasing to the consumer.

Antiperspirant compositions are available in a variety of forms, such as aerosol suspensions; pump sprays; roll-on powders; emulsions or suspensions; and solid gels, waxes or suspensions. Antiperspirant compositions traditionally have been prepared as either oil-in-water emulsions or water-in-oil emulsions. Therefore, antiperspirant compositions of any form typically have a milky or opaque appearance and are manufactured by complex methods. Antiperspirant compositions prepared as emulsions often feel wet or oily when applied to the skin, and often remain tacky after the carrier of the composition evaporates. In addition, many emulsion-type antiperspirant compositions leave a white, staining residue on contacted skin or clothing.

Roll-on and gelled emulsion-type antiperspirant compositions are used by rubbing an area of the body, such as the underarm, to apply a layer of the composition to the skin, and thereby reduce odor and/or perspiration. Roll-on and gel antiperspirant compositions preferably possess the esthetic properties of smoothness, nonoiliness and nontackiness. Gelled antiperspirant compositions also require a sufficient firmness to maintain its shape. Clarity, or transparency, of antiperspirant compositions also is a long-sought desirable esthetic property. Another highly desirable, but hard to achieve, esthetic property is avoiding a visible residue, e.g., a white layer, that is left on the skin or clothing after the antiperspirant composition is applied.

Nonemulsified antiperspirant compositions also are known in the art. However, nonemulsified compositions often require shaking prior to each use in order to redisperse the insoluble antiperspirant compound that has separated from the composition. Nonemulsified antiperspirant compositions that do not require shaking prior to each use, such as an antiperspirant creme or paste, typically include a relatively high percentage of suspending agents, like an organoclay. The presence of an organoclay in an antiperspirant composition is a principal source of the whitening and staining of skin and clothing.

Investigators have searched for antiperspirant compositions, and especially transparent antiperspirant compositions, that display the above-listed desirable properties. A roll-on antiperspirant is difficult to formulate and manufacture because the composition requires a sufficient viscosity to adhere to the skin, resists dripping off or running down the skin, and yet is not tacky or sticky. A gel antiperspirant composition is difficult to formulate and manufacture because the composition requires sufficient firmness to withstand rubbing across the skin to deliver a sufficient amount of the antiperspirant compound to the skin. Additional formulation parameters include viscosity control, lack of syneresis and nontackiness. Transparent, roll-on or gel antiperspirant compositions are more difficult to formulate because of the added requirement of transparency.

A transparent roll-on or gel antiperspirant composition which has esthetic and functional properties equal to or better than presently-available antiperspirant compositions is highly desired by consumers. However, providing a commercially-acceptable, transparent roll-on or gel antiperspirant composition requires overcoming several formulation and manufacturing problems.

Transparent antiperspirant compositions, especially in the roll-on or gel form, are particularly favored by consumers because such transparent products are esthetically-appealing and project the appearance of product purity, safety, good performance and being non-whitening. However, due to the instability and the difficult manufacture of transparent compositions, transparent antiperspirant compositions are not readily available to consumers.

Solid antiperspirant compositions are divided into three main classes, i.e., compressed powder sticks, gel sticks and wax sticks. Each of these classes has advantages, but each class also has particular disadvantages. Compressed powder sticks for example are frequently brittle and hard, and leave a cosmetically-unacceptable powdery residue after application. Frequently, wax-based products are cosmetically unacceptable because of such factors as hardness, greasiness and tackiness. The opacity of wax sticks and the visually-observable white residue remaining after application also are esthetically undesirable.

Gel-type solid antiperspirant compositions have several advantages over both compressed powder sticks and wax sticks. For example, the gel antiperspirant compositions leave less residue or dust on the skin. The gel antiperspirant compositions also glide easily over the skin surface resulting in an easy and comfortable application of the composition.

However, the preparation of antiperspirant compositions in the form of an effective and stable gel is difficult. For example, a critical ingredient in gel antiperspirant compositions is the gelling agent. Many prior gel antiperspirant compositions comprise gelled hydroalcoholic solutions including a gelling agent, such as sodium stearate, to form the gel. However, common gelling agents cannot be used in the presence of acidic antiperspirant compounds because of an interaction between the gelling agent, which is alkaline, and the antiperspirant compound.

Prior transparent, gel antiperspirant compositions also typically were divided into three main classes. One of these classes is the optically-clear gelled emulsion compositions. These compositions include a water phase and an oil phase. The oil phase is suspended in the water phase by using a sufficient amount of an appropriate emulsifier or emulsifiers. The emulsions conventionally contained waxes, silicones, clays and emollients. The optically-clear gelled emulsion compositions are illustrated in U.S. Pat. Nos. 4,673,570, 4,268,499, 4,278,655, and 4,350,605; EP 0 450 597; and in "Deodorant and Antiperspirant Formulary", *Cosmetics & Toiletries,* Dec. 12, 1985, vol. 100, p. 65–75.

The optically-clear gelled emulsion compositions often exhibit the disadvantages of composition instability during storage; the development of a hazy or milky appearance during storage; a stringy, tacky, oily consistency and other undesirable esthetics. In addition, the emulsion gel compositions often leave a visible residue, in the form of a white layer, on the skin or clothing. Another disadvantage of optically-clear gelled emulsion compositions is the complex method of preparing an optically-clear gelled emulsion composition. The method traditionally requires high shear rates during mixing, high processing temperatures, and a series of cooling and heating process steps. In one embodiment of the present invention, optically-clear gelled emulsion compositions are prepared by a simple method to provide antiperspirant compositions that overcome the above-described disadvantages of optically-clear gelled emulsion compositions.

A second class of transparent gel antiperspirant compositions is antiperspirant compositions thickened with 1,3:2,4-dibenzylidene-sorbitol (DBS) or DBS derivatives. Such transparent antiperspirant compositions are disclosed in U.S. Pat. Nos. 4,822,602 and 4,725,430; European Patent Publication 0 512 770; WO 91/15191; and WO 92/19222.

Transparent, gelled antiperspirant compositions thickened with DBS or DBS-type compounds have a major disadvantage in that the compositions are unstable in the presence of highly-acidic antiperspirant compounds at elevated temperatures. In addition, another disadvantage is the high temperature required for manufacturing DBS-thickened compositions (i.e., about 230° F. to about 240° F.).

The third class of transparent gel antiperspirant compositions is the acid-base complex gels. These transparent antiperspirant compositions are prepared by interacting the active antiperspirant compound with a carboxylic acid salt. Transparent acid-based complex gels are disclosed, for example, in U.S. Pat. Nos. 3,255,082 and 2,876,163; and in European Publication No. 0 448 278. U.S. Pat. Nos. 2,607,658 and 2,645,616 disclose similar gels comprising an aluminum chlorhydroxy complex and a borate.

For example, EP 0 448 278 discloses complexing an antiperspirant aluminum salt with ammonium acetate. U.S. Pat. No. 2,876,163 discloses complexing an antiperspirant aluminum salt with various water-soluble inorganic salts, like an alkali metal oxide, hydroxide, or carbonate, or a salt of an organic or inorganic acid, such as sodium carbonate, sodium phosphate, or sodium glutamate.

This third class of transparent antiperspirant compositions has a major disadvantage in that the active antiperspirant compound is partially deactivated by the salt, thereby reducing the efficacy of the antiperspirant compound and, accordingly, the antiperspirant composition. In addition, the resulting gels are very brittle, tacky, and/or possess other undesirable esthetic properties, such as in the compositions disclosed in U.S. Pat. No. 3,255,082, which are emulsions or sols and therefore are often opaque.

The problems associated with gel antiperspirants can be partially overcome by formulating a roll-on antiperspirant. Roll-on antiperspirants typically are viscous liquids to semisolids. However, roll-on antiperspirants often impart a tacky feel and still have the ability leave an unsightly white residue on the skin.

Although numerous patents disclose transparent gel antiperspirant compositions, the gel compositions designated as clear or transparent do not have the clarity desired by consumers. Some transparent antiperspirant compositions also exhibit syneresis, or phase separation, during storage. Moreover, many of the prior art transparent compositions become cloudy or hazy after standing for a period of time. Typically, haziness increases to such an extent that the composition is cloudy and has little or no transparency about a month after preparation. Antiperspirant compositions conventionally have a product life in excess of one month. Therefore, the length of time the composition retains its transparency is an important esthetic property.

Investigators have continually sought to provide roll-on or gel antiperspirant compositions having both long-term stability and sufficient esthetic and functional properties for consumer acceptance. These esthetic and functional properties include transparency, a sufficient firmness for application to the skin, no visually-observable whitening of the skin and clothing, and the ability to effectively deliver the antiperspirant compound to the skin without providing a tacky or sticky feeling. The present invention is directed to providing roll-on or gel antiperspirant compositions, and preferably transparent compositions, exhibiting these consumer-acceptable esthetic and functional properties.

SUMMARY OF THE INVENTION

The present invention relates to roll-on or gel antiperspirant compositions having improved efficacy and esthetics, and to methods of using the antiperspirant compositions. More particularly, the present invention is directed to a transparent, roll-on or gel antiperspirant composition comprising an antiperspirant compound; a hydrophilic polymer; a carrier; and, optionally, a softening agent.

In particular, the roll-on or gel or solid antiperspirant compositions comprise:

(a) about 1% to about 40% by weight of an antiperspirant compound, like an astringent salt;

(b) about 0.005% to about 10% by weight of a hydrophilic polymer, like a hydrophilic polyurethane having a weight average molecular weight of at least about 10,000;

(c) a carrier; and (d) optionally, 0% to about 15% by weight of a softening agent, like a nonionic surfactant. The transparent antiperspirant compositions are acidic in nature, having a pH of about 2 to about 6.

The transparent, roll-on or gel antiperspirant compositions maintain composition clarity over extended storage periods, are essentially nonstaining and nonwhitening to skin and clothing, effectively deliver the antiperspirant compound to the skin, and exhibit excellent esthetic and functional properties, including sensory properties, for consumer acceptance. The present antiperspirant compositions remain transparent for at least six months when stored at room temperature.

In a preferred embodiment, the transparent roll-on or gel antiperspirant composition comprises:

(a) about 5% to about 30% by weight of an aluminum or zirconium astringent salt, or combination thereof;

(b) about 0.1% to about 5% by weight of a hydrophilic polymer selected from the group consisting of an ethoxylated, propoxylated or carboxylated hydrophilic polyurethane having a weight average molecular weight of at least about 20,000, a polyethylene glycol having a weight average molecular weight of at least 100,000, a water-soluble cellulosic polymer, and mixtures thereof;

(c) a carrier; and (d) optionally, 0% to about 12% by weight of a nonionic surfactant, wherein the transparent antiperspirant composition has a pH of about 3 to about 5.

In another preferred embodiment, the transparent, roll-on or gel antiperspirant compositions include a hydrophobic compound to improve a particular esthetic or functional property of the antiperspirant compound. The hydrophobic compound can be a siloxane or a hydrocarbon, for example, and is included in the transparent antiperspirant composition in an emulsified form.

The present invention also relates to a method of treating or preventing malodors associated with human perspiration, especially underarm odor. The method comprises topically applying an effective amount of a roll-on or gel antiperspirant composition of the present invention to the skin of a human.

The above and other advantages and novel features of the present invention will become apparent from the following detailed description of the preferred embodiments of the invention.

DETAILED DESCRIPTION OF THE PREFERRED EMBODIMENTS

A roll-on or gel antiperspirant composition of the present invention comprises an antiperspirant compound, a hydrophilic polymer, a carrier, and, optionally, a softening agent. In particular, the roll-on or gel antiperspirant compositions have a pH of about 2 to about 6 and comprise:

(a) about 1% to about 40% by weight of an antiperspirant compound;

(b) about 0.005% to about 10% by weight of a hydrophilic polymer;

(c) a carrier; and (d) optionally, 0% to about 15% by weight of a softening agent, such as a surfactant. Typically, the antiperspirant compositions are transparent. As used here and hereinafter, the term "transparent" is defined as at least 50% transmittance determined spectrophotometrically at 700 nm (nanometers).

The transparent roll-on or gel antiperspirant compositions are stable to phase separation, do not become hazy or milky during storage, and exhibit exceptional esthetic and functional properties. The antiperspirant compositions are firm, nonstringy and nontacky, and are capable of effectively delivering the antiperspirant compound to the skin, without leaving a visually-observable white residue on the skin or clothing, i.e., are essentially nonwhitening.

The present roll-on or gel antiperspirant compositions incorporate any of the antiperspirant compounds known in the art, such as the astringent salts. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6.

Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2-nz is greater than or equal to 0; and L is selected from the group consisting of halides, nitrate, sulfamate, sulfate, and mixtures thereof.

The antiperspirant compound is present in the gelled antiperspirant composition in an amount of about 1% to about 40%, and preferably about 5% to about 30%, by weight of the composition. To achieve the full advantage of the present invention, the antiperspirant compound is present in an amount of about 10% to about 25% by weight of the antiperspirant composition.

The antiperspirant compounds are water-soluble. Exemplary antiperspirant compounds therefore include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the *Cosmetic and Toiletry Fragrance Handbook,* The Cosmetic, Toiletry and Fragrance Association, Inc., Washington, DC, p. 56, 1989, hereinafter the *CTFA Handbook,* incorporated herein by reference.

Preferred antiperspirant compounds are the aluminum-zirconium chlorides complexed with an amino acid, like glycine, and the aluminum chlorohydrates. Preferred aluminum-zirconium chloride glycine complexes have an aluminum (Al) to zirconium (Zr) ratio of about 1.67 to about 12.5, and a total metal (Al+Zr) to chlorine ratio (metal to chlorine) of about 0.73 to about 1.93. These antiperspirant compounds typically are acidic in nature, thereby providing a gelled antiperspirant composition having a pH less than 7, and typically having a pH of about 2 to about 6, and preferably about 3 to about 5.

In addition to the antiperspirant compound, a roll-on or gel antiperspirant composition of the present invention also includes about 0.005% to about 10%, and preferably about 0.01% to about 5%, by weight of the composition, of a hydrophilic polymer. To achieve the full advantage of the present invention, the hydrophilic polymer is present in an amount of about 0.1% to about 3%, by weight of the composition.

The hydrophilic polymer has a molecular weight of at least about 5,000. The hydrophilic polymer also tolerates a pH of about 2 to about 6, and resists precipitation from solution in the presence of a relatively high salt concentration. Therefore, the hydrophilic polymer is either a hydrophilic ionic polymer having a low charge density (e.g., an anionic polymer having a limited number of carboxyl groups) or, preferably, a nonionic polymer. The hydrophilic polymer acts as a viscosity modifier or thickener, and does not contribute to whitening of skin or clothing.

A roll-on or gel antiperspirant composition including an antiperspirant compound, like an aluminum chlorohydrate, and a hydrophilic polymer is a transparent, viscous or gelled composition. The viscosity and gel consistency can be adjusted to provide a commercially-acceptable product.

A polymer included in a transparent antiperspirant composition of the present invention is hydrophilic, and therefore is soluble or dispersible in polar liquids, like water, alcohols, glycols and polyols. As will be described in more detail hereinafter, such polar liquids are carriers of the antiperspirant compositions of the present invention. The hydrophilic polymer also is soluble in, and does not precipitate from, a polar liquid in the presence of a relatively high salt concentration and at a pH of about 2 to about 6.

Exemplary hydrophilic polymers include, but are not limited to, polyethylene glycols, polypropylene glycols, polyacrylamides, polymethacrylamides, polyvinyl alcohols, polyvinyl pyrrolidones, dimethicone copolyols, alkyl dimethicone copolyols, water-soluble cellulosic polymers, hydroxypropylmethylcellulose, hydroxyethyl cellulose, hydroxybutylmethylcellulose, carboxymethylcellulose, polyoxyethylenepolyoxypropylene copolymers, polyurethanes, and mixtures thereof, as long as the hydrophilic polymer is water soluble or water dispersible, and has a weight average molecular weight of at least about 5,000. The weight average molecular weight of the hydrophilic polymer can range from about 5,000 to about 5,000,000.

An especially useful class of hydrophilic polymers is the hydrophilic polyurethanes having a weight average molecular weight of at least about 10,000, and preferably about 20,000 to about 300,000. A weight average molecular weight in excess of 300,000 is not detrimental, but hydrophilic polyurethanes of molecular weight greater than 300,000 are difficult to handle and disperse in the carrier of the antiperspirant composition.

The hydrophilic polyurethanes typically are ethoxylated and/or propoxylated at least at one terminal end, and are terminated with a hydroxyl group. Another class of useful hydrophilic polyurethanes is the carboxylated polyurethanes having a low charge density.

The hydrophilic polyurethanes can be prepared from an aliphatic diisocyanate, an aromatic diisocyanate, or a mixture thereof. An aliphatic diisocyanate is preferred. The diisocyanate is typically interacted with a low molecular weight glycol or triol, such as ethylene glycol, diethylene glycol, propylene glycol, glycerol, hexylene glycol, dipropylene glycol, or mixtures thereof, wherein the glycol or triol has at least two hydroxyl groups and a molecular weight up to about 200 to provide a polyurethane. The diisocyanate also can be reacted with a polymeric dihydroxy-terminated oligomer having a molecular weight of about 200 to 10,000 to provide a hydrophilic polyurethane. Exemplary oligomers include, but are not limited to polypropylene glycols, polyethylene glycols, polybutylene glycols, and mixtures thereof. Preferably, a diisocyanate is interacted both with a low molecular weight diol or triol and with an oligomer to provide a hydrophilic polyurethane.

Exemplary, but non-limiting, diisocyanates include trimethylhexamethylene diisocyanate, isophorone diisocyanate, decamethylene-1,10-diisocyanate, cyclohexane-1,2-diisocyanate, methylene bis(cyclohexyl-4-isocyanate), toluene-1,4-diisocyanate, toluene-2,6diisocyanate, diphenylmethane-4,4'-diisocyanate, 3,3'-dimethyldiphenylmethane-4,4'-diisocyanate, m-phenylene diisocyanate, p-phenylene diisocyanate, chlorophenylene diisocyanate, hexamethylene-1,6-diisocyanate, tetramethylene-1,4-diisocyanate, cyclohexane-1,4-diisocyanate, naphthalene-1,5-diisocyanate, 1-methoxyphenyl-2,4-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dichlorophenyl-4,4'-diisocyanate, 2,2',5,5'-tetrachlorodiphenyl-4,4'-diisocyanate, trimethylhexamethylene diisocyanate, m-xylene diisocyanate, and mixtures thereof. The polyurethane backbone also can be substituted with hydroxyl or carboxyl groups to improve the water solubility or dispersibility of the hydrophilic polymeric binder. Preferred hydrophilic polyurethanes are disclosed in Gould et al. U.S. Pat. No. 5,000,955, incorporated herein by reference. Other useful hydrophilic polyurethanes are disclosed in U.S. Pat. Nos. 3,822,238; 4,156,066; 4,156,067; 4,255,550; and 4,743,673, also incorporated herein by reference.

Other useful classes of hydrophilic polymers are the dimethicone copolyols and the alkyl dimethicone copolyols. These hydrophilic polymers have advantages such as being liquid at room temperature, being water soluble or dispersible, and being easily incorporated into the antiperspirant compositions of the present invention. In addition, because of their amphiphilic nature, these polymers provide good skin feel properties.

In particular, the alkyl dimethicone copolyols have the structural formula

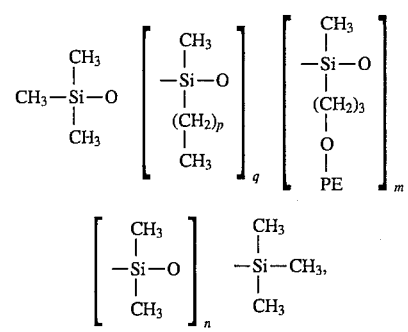

wherein p is a numeral from 0 through 24;

q is a numeral from 1 through 100;

m is a numeral from 1 through 40;

n is a numeral from 0 through 200; and

PE is $(C_2H_4O)_a(C_3H_6O)_b$-H having a molecular weight of about 250 to about 2000, wherein a and b are selected such that the weight ratio of $C_2H_4O/C_3H_6O$ is from 100/0 to 20/80. The alkyl dimethicone copolyols have a viscosity of about 1 to about 1,000 centipoise (cps).

An exemplary, but nonlimiting, alkyl dimethicone copolyol is cetyl dimethicone copolyol available commercially as ABIL® EM 90 from Goldschmidt Chemical Corporation, Hopewell, Va.

A dimethicone copolyol also can be used as the hydrophilic polymer. A dimethicone polyol is a dimethylsiloxane polymer having polyoxyethylene and/or polyoxypropylene side chains, such as DOW CORNING 3225C FORMULATION AID, available from Dow Corning Co., Midland, Mich., AMERSIL DMC-357, available from Amerchol Corp., Edison, N.J. or ABIL® B8852, available from Goldschmidt Chemical Corporation, Hopewell, Va.

Dimethicone copolyols have the structural formula

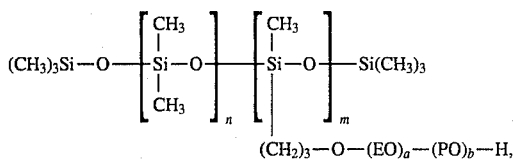

wherein EO is ethylene oxide ($C_2H_4O$), PO is propylene oxide ($C_3H_8O$), a and b are selected such that the weight ratio of EO/PO is 100/0 to 20/80, n is a numeral from 0 through 200, and m is a numeral from 1 through 40. The dimethicone copolyols have a viscosity of about 1 to about 600 centipoise.

The carrier of the present roll-on or gel antiperspirant composition comprises water, water-soluble solvents and mixtures thereof. Exemplary carriers include, but are not limited to, water, ethylene glycol, propylene glycol, butylene glycol, propylene carbonate, dimethyl isosorbide, hexylene glycol, ethanol, n-butyl alcohol, n-propyl alcohol, isopropyl alcohol, and mixtures thereof. The carrier is present in a sufficient amount to solubilize, disperse or hydrate the essential and optional ingredients of the transparent antiperspirant composition.

As will be discussed in detail hereinafter, the transparent antiperspirant composition also can include a water-insoluble, or hydrophobic, compound, such as isohexadecene or 1-decene dimer, as long as a sufficient amount of an emulsifier also is included to emulsify the water-insoluble compound. Such water-insoluble compounds are not present as a carrier of the composition, but are included as optional ingredients for a specific purpose, such as faster drying time, better skin feel, or ease of application.

The present roll-on or gel antiperspirant compositions also can include an optional softening agent. The softening agent ensures efficacious delivery of the antiperspirant composition to the skin. The softening agent is present in the antiperspirant composition in an amount of 0% to about 15%, and preferably 0% to about 12%, by weight of the composition. The softening agent is a water-soluble compound, and typically is classified as an emollient or a surfactant.

Therefore, exemplary softening agents include, but are not limited to, polyoxyethylene ethers of fatty ($C_6$–$C_{22}$) alcohols, polyoxypropylene ethers of fatty ($C_6$–$C_{22}$) alcohols, dimethicone copolyols, polypropylene glycols, polyethylene glycols, ethoxylated alkylphenols, polyethylene glycol ethers of methyl glucose and mixtures thereof. The softening agents have an HLB (hydrophilic-lipophilic balance) value of at least about 6, and preferably at least about 8, and a weight average molecular weight of less than about 10,000, and preferably less than about 5,000. The HLB system of classifying surfactants is well-known to persons skilled in the art.

Specific, softening agents include methyl gluceth-20, methyl gluceth-10, $C_{12-15}$ alkyl benzoates, PEG-20 methyl glucose distearate, PEG-20 methyl glucose sesquistearate, PEG-200 castor oil, PEG-6, PEG-8, $C_{11-15}$ pareth-20, nonoxynol-9, octoxynol-10, nonyl nonoxynol-10, ceteth-8, ceteth-12, dodoxynol-12, laureth-15, PEG-20, PEG-3 castor oil, PEG-8 castor oil, PEG-20 castor oil, poloxamer 101, polysorbate 20, PPG-11 stearyl ether, dimethicone copolyol, steareth-20, and mixtures thereof. Other useful water-soluble softening agents are listed in the *CTFA Handbook* at pages 87 through 94, incorporated herein by reference.

In addition to the essential ingredients and the optional softening agent, the present roll-on or gel antiperspirant compositions also can include other optional ingredients traditionally included in antiperspirant compositions. These optional ingredients include, but are not limited to, dyes, fragrances, preservatives, antioxidants, detackifying agents, deodorizing agents, and similar types of compounds. These optional ingredients typically are included in the antiperspirant composition in an amount of about 0.01% to about 10% by weight of the composition.

The present roll-on or gel antiperspirant compositions typically are transparent. However, opacifying agents, pearlescent agents or fillers (e.g., titanium dioxide or a styrene-acrylamide copolymer) that render the antiperspirant composition nontransparent also can be included in the composition. The presence of such ingredients does not adversely effect the efficacy of the composition and are added to achieve a desired esthetic effect. Preferably, however, the antiperspirant composition is transparent, and typically is transparent unless rendered opaque by an intentionally-added optional ingredient.

In addition, a hydrophobic compound optionally can be included in the transparent antiperspirant compositions, as long as the hydrophobic compound is sufficiently emulsified in the antiperspirant composition. The hydrophobic compound can be, for example, an aliphatic hydrocarbon, a fatty alcohol benzoate ester, a fatty ($C_8$–$C_{12}$) alcohol or a siloxane. These hydrophobic compounds improve the feel of the antiperspirant composition on the skin, allow easier application of the antiperspirant composition to the skin, and allow the skin to dry faster after application of the antiperspirant composition. The hydrophobic compounds are emulsified by compounds and methods well-known to those skilled in the art. Preferably, the hydrophobic compound is emulsified in a manner known to those skilled in the art to provide a transparent antiperspirant compound.

Hydrophobic aliphatic hydrocarbons incorporated into the transparent antiperspirant composition include, for example, isohexadecane, 1-decene dimer, mineral oils, nonvolatile hydrocarbon fluids, and hydrocarbons depicted in general structural formula (I), wherein n ranges from 2 to 5,

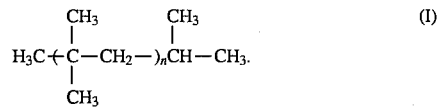

Volatile hydrocarbons, such as a hydrocarbon including about 10 to about 30 carbon atoms, have sufficient volatility to slowly volatilize from the skin after application of the antiperspirant composition. The volatile hydrocarbons provide benefits such as lubrication, a rich feel during application and faster drying. Specific volatile hydrocarbons having the structural formula (I) are the commercially-available compounds PERMETHYL 99A and PERMETHYL 101A, corresponding to compounds of general structure (I) wherein n is 2 and 3, respectively, available from Permethyl Corporation, Pottstown, Pa.

Siloxanes included in the transparent antiperspirant compositions provide the same benefits as the aliphatic hydrocarbons. Exemplary siloxanes include phenyltrimethicone; cyclic or linear, low molecular weight, volatile polydimethylsiloxanes known as cyclomethicones and dimethicones, respectively; and methicones. The cyclomethicones are low viscosity, low molecular weight, water-insoluble cyclic compounds having an average of about 3 to about 6—[O—$Si(CH_3)_2$]—repeating group units per molecule. Cyclomethicones are available commercially under the tradenames SILICONE 344 FLUID and SILICONE 345 FLUID from Dow Corning Corporation, Midland, Mich., and SILICONE SF-1173 and SILICONE SF-1202 from General Electric, Waterford, N.Y., for example.

An example of a linear, low molecular weight, volatile dimethicone is the compound hexamethyldisiloxane, available commercially under the tradename DOW CORNING 200 FLUID, from Dow Corning Corp., Midland, Mich. DOW CORNING 200 FLUID has a viscosity of 0.65 cs (centistokes), is highly volatile, is non-greasy, provides lubrication for topical application of the composition of the present invention to the skin. Other linear polydimethylsiloxanes, such as tributoxypropyltrisiloxane, decamethyltetrasiloxane, octamethyltrisiloxane, and dodecamethylpentasiloxane, also have sufficient volatility to provide a dry feel after application. Another useful linear siloxane is bisphenylhexamethicone. Nonvolatile siloxanes also can be used as the hydrophobic compound. The volatile siloxanes and aliphatic hydrocarbons can be used alone, in combination, or in combination with nonvolatile siloxanes and/or nonvolatile aliphatic hydrocarbons.

Other suitable hydrophobic compounds include waxes, oils and fats, and water-insoluble emollients, like fatty ($C_8$–$C_{22}$) alcohols. The hydrophobic compounds are emulsified by including an emulsifying surfactant in the composition. Typically, the emulsifying surfactant is a nonionic surfactant. The particular amount and identity of the emulsifying surfactant can be determined by a person skilled in the art after considering the identity and amount of hydrophobic compound included in the composition. Typical emulsifying surfactants are listed in the CTFA Handbook at page 87 through 94, incorporated herein by reference.

To demonstrate the roll-on or gel antiperspirant compositions of the present invention, the following nonlimiting examples were prepared. In some cases, the composition of a particular example was compared to other examples or to a present day commercial antiperspirant product for an esthetic or functional property. It was found that an antiperspirant composition of the present invention leaves essentially no white residue, i.e., leaves no visually-observable white residue. Such a result is surprising because a white residue, attributable to the solid antiperspirant compound, typically is observed after other antiperspirant composition ingredients evaporate. In addition to being nonwhitening, the present antiperspirant compositions have the added esthetic benefit of being transparent. Heretofore, transparency has been difficult to achieve in roll-on or gel antiperspirant compositions because the gelling agents either interacted with the antiperspirant compound or were ineffective at a low pH of about 2 to about 6.

In accordance with another important feature of the present invention, the transparent roll-on or gel antiperspirant compositions of the present invention are manufactured by simply admixing composition ingredients at a relatively low temperature. Contrary to prior methods of manufacturing roll-on or gel antiperspirant compositions, the elevated temperatures needed to melt the thickening agents, and the long cooling times to provide the antiperspirant composition, are not required.

An antiperspirant composition of the present invention is prepared by introducing a portion of the carrier and the hydrophilic polymeric binder into a first vessel. The resulting mixture is mixed, mildly at a temperature of about 20° C. to about 45° C., until homogeneous. Then, the softening agent and all other optional ingredients are added to the first vessel, in any order, and agitation is continued until the resulting mixture is homogeneous. In a second vessel, the antiperspirant compound and the remaining portion of the carrier are admixed, then heated to about 40° C. to about 45° C. and stirred until homogeneous. Next, the homogeneous mixture in the first vessel is slowly added to the homogeneous solution in the second vessel. The resulting mixture is stirred until homogeneous, and the resulting solution is poured into a suitable antiperspirant container and allowed to cool to room temperature. The antiperspirant composition is transparent unless an intentionally-added optional ingredient provides an opaque or pearlescent composition.

As will be demonstrated in the following examples, the antiperspirant compositions were transparent and phase-stable over the life of the product; were viscous (roll-on) or firm (gel); were easy to apply and effectively delivered the antiperspirant compound to the skin; and did not whiten the skin or clothing. Each of the following examples was prepared by the above-described method.

EXAMPLE 1

| Ingredient | Example 1[1] |
| --- | --- |
| Antiperspirant Compound[2] | 12.5 |
| Hydrophilic polymer[4] | 2.0 |
| Water[3] | 85.5 |

[1] the amount of each ingredient is expressed as % by weight of the total composition, all percents set forth the amount of each ingredient present in the composition;
[2] aluminum chlorohydrate (ACH), available commercially as CHLOROHYDROL, from Reheis, Inc. Berkeley Heights, New Jersey, added as a 50% weight percent solution of ACH in water;
[3] carrier; and
[4] AMERCELL™ Polymer HM-1500, a nonionic, water-soluble, hydrophobically-modified hydroxyethyl cellulose having a molecular weight greater than 50,000, available commercially from Amerchol Corp., Edison, NJ.

The composition of Example 1 was a slightly hazy, pale yellow, flowable gel-like composition which spread easily on the skin and dried quickly, leaving behind a film. The composition of Example 1 had a very slight tack. The composition of Example 1 was phase stable and phase reversible at 25° C. and 50° C., and was stable to freeze thaw cycles. The composition of Example 1 did not leave a visible white residue on the skin.

Compositions including a relatively low amount of antiperspirant compound are termed deodorants as opposed to antiperspirants. Deodorant compositions also can be made consumer acceptable by incorporating an appropriate amount of hydrophilic polymeric binder into the composition.

Accordingly, a sufficient amount of hydrophilic polymer in the composition provides a roll-on to gel composition of desired consistency. The necessary amount of hydrophilic polymer to provide a desired composition varies with the amount of antiperspirant compound in the composition.

An antiperspirant composition of the present invention has a viscosity of about 30 to about 200,000 cps (centipoises). For a roll-on antiperspirant composition, a sufficient amount of hydrophilic polymer is present in the antiperspirant composition if the composition has a viscosity of at least about 30 cps (centipoise), and preferably about 100 to about 3000 cps, and effectively overcomes the tendency of the antiperspirant compound to leave a visible white residue on the skin. A more preferred viscosity for a roll-on antiperspirant composition is about 200 to about 3000 caps.

For a gel antiperspirant composition, a sufficient amount of hydrophilic polymeric binder is present in the antiperspirant composition if the composition has a viscosity of about 50,000 to about 200,000 cps, and preferably about 50,000 to about 100,000 cps (as measured on a Brookfield Viscometer with a #6 spindle at 5 rpm), and effectively overcomes the tendency of the antiperspirant composition to leave a visible white residue on the skin. The viscosity range of about 3,000 to about 50,000 cps provides a useful antiperspirant composition but lacks some of the esthetic properties consumers consider important.

An important feature of the present invention is reduction of the white residue on skin and clothing resulting from the use of an antiperspirant composition. The absence of a white residue is a primary esthetic property desired by consumers in antiperspirant compositions.

Present-day roll-on and gel antiperspirants leave a cosmetically-unacceptable white residue on the skin or clothing after application to the skin. The present compositions incorporating a hydrophilic polymer in roll-on or gel antiperspirant compositions have a consumer acceptable firmness or viscosity and also reduce the white residue on skin and clothing.

The following compositions of Examples 2–5 demonstrate that incorporating a hydrophilic polymer in roll-on or gel antiperspirant compositions leaves no visually-observable white residue on the skin. The compositions of Examples 2 and 3 were identical, except 1% by weight of a hydrophilic polyurethane resin, having a weight average molecular weight of about 248,000 and an NCO/OH ratio of 0.98, was incorporated into the composition of Example 3. The composition of Example 4 is a commercial roll-on antiperspirant formulation, wherein the bentone is omitted. Bentone is an ingredient in the commercial roll-on composition used as a suspending agent.

The composition of Example 5 is similar to the composition of Example 4 except 4% by weight of the hydrophilic polyurethane resin incorporated into the composition of Example 3 and 1% by weight of a hydrophilic polyurethane having a weight average molecular weight about 159,000 and an NCO/OH ratio of 0.98 were incorporated into the composition of Example 5. The compositions of Examples 2–5 were compared to a present-day, commercial antiperspirant composition (DEGREE UNSCENTED, available from Helene Curtis, Inc., Chicago, Ill.) for the degree of whitening imparted to a substrate.

| Ingredients | Example 2[1] (comparative) | Example 3 | Example 4 (comparative) | Example 5 |
|---|---|---|---|---|
| Antiperspirant Compound | 25.0[16] | 25.0[16] | 22.0[9] | 22.0[9] |
| Hydrophilic Polymer | — | 1.0[8] | — | 5.0[14] |
| Carrier | 87.5[5] | 86.5[6] | 0.75[7] | 0.75[7] |
| Cyclomethicone | — | — | 71.5[10] | — |
| Dimethicone | — | — | — | 65.75[15] |
| Aluminum Starch Octenylsuccinate | — | — | 0.5[11] | 0.5 |
| Silica | — | — | 0.25[12] | 0.25 |
| Dioctyl adipate | — | — | 5.0[13] | 5.75 |

[5]70% propylene carbonate and 5% hexylene glycol;
[6]69% propylene carbonate and 5% hexylene glycol;
[7]0.75% propylene carbonate;
[8]a hydrophilic polyurethane resin having a weight average molecular weight of about 248,000, an NCO/OH ratio of 0.98, and prepared in accordance with the method of Examples 1–5 of U.S. Pat. No. 5,000,955, incorporated herein by reference;
[9]aluminum zirconium glycinate (AZG) available commercially as REZAL 36GPG, from Reheis, Inc., Berkeley Heights, New Jersey, added as a 100% weight percent active material;
[10]SILICONE 344 FLUID, available from Dow Corning Corp., Midland, MI, added as a 100% active material;
[11]added as a 100% active material;
[12]added as a 100% active material;
[13]added as a 100% active material;
[14]4% by weight of a hydrophilic polyurethane resin having a weight average molecular weight of about 248,000 and an NCO/OH ratio of 0.98; and 1% by weight of a hydrophilic polyurethane resin having a weight average molecular weight of about 159,000 and an NCO/OH ratio of 0.98; each made in accordance with the methods of Examples 1–5 of U.S. Pat. No. 5,000,955, incorporated herein by reference;
[15]DIMETHICONE 200 FLUID, available from Dow Corning Corp., Midland, MI, added as 100% active material; and
[16]ACH Powder 323, an unpalpable solid, available commercially from Dow Corning Corporation, Midland, MI, added as a 100% active material.

The compositions of Examples 2–5 and DEGREE were tested for whitening by individually applying 0.5 ml (milliliter) of each composition to a blackboard. Each composition was spread evenly on the blackboard with a doctor blade. The white residue left by each composition of Examples 2–5 and DEGREE was measured at minutes and at 2 hours after application with a chromometer.

The results of the chromometer measurements are summarized in Table 1.

The chromometer measurements summarized in Table 1 show that after 30 minutes the relative amount of white residue left on the blackboard by each composition was:

TABLE 1

Chromometer Measurements for Antiperspirant Compositions

|  | After 30 minutes | After 2 hours |
|---|---|---|
| Example 2 | 14.75 | 33.43 |
| Example 3 | 19.16 | 22.53 |
| Example 4 | 37.24 | 64.85 |
| Example 5 | 22.13 | 26.31 |
| DEGREE UNSCENTED | 30.59 | 63.93 |

(no visually-observable whitening) Ex. 2 < Ex. 3 < Ex. 5 << DEGREE < Ex. 4 (very white)
After 2 hours, the relative amount of white residue left on the blackboard by each composition was:
(no visually-observable whitening) Ex. 3 < Ex.5 << Ex. 2 << DEGREE < Ex. 4 (very white)

Therefore, the composition of Example 4, which does not include a hydrophilic polymeric binder, left the greatest amount of white residue both 30 minutes and 2 hours after application. The composition of Example 5, incorporating a hydrophilic polymer, left a substantially lower white residue. After two hours of drying, the compositions of Examples 3 and 5, each incorporating a hydrophilic polymer outperformed all other antiperspirant compositions, including the present day commercial product.

The antiperspirant compositions of the present invention also can incorporate a softening agent. The softening agent improves the ability of the transparent, roll-on or gel antiperspirant composition to deliver the antiperspirant compound to the skin. The antiperspirant compositions including a softening agent were roll-on or gel products having excellent esthetic and functional properties, including an improved ability to deliver the antiperspirant compound to the skin. A judicious selection of the amount and identity of the softening agent maintains the transparency of the antiperspirant composition. The determination of the identity and amount of softening agent necessary to maintain composition transparency is readily determined by a person skilled in the art.

In accordance with an important feature of the present invention, the transparent roll-on or gel antiperspirant compositions also can incorporate an emulsified hydrophobic compound and maintain composition transparency, efficacy and esthetics. Such antiperspirant compositions therefore include a polar phase, an oil phase and at least one emulsifier. The polar phase comprises the antiperspirant compound, water, propylene glycol, other hydrophilic carriers, the hydrophilic polymeric binder and any other water-soluble or water-dispersible optional ingredients, including the softening agent.

The oil phase includes the hydrophobic compound, such as, for example, hydrocarbon oils, volatile and nonvolatile hydrocarbon fluids, volatile cyclic dimethylsiloxanes, volatile and nonvolatile linear dimethylsiloxanes, waxes, and saturated and unsaturated oils and fats, and water-insoluble emollients, such as fatty ($C_8$–$C_{22}$) alcohols. The oil phase conventionally includes volatile or low viscosity hydrocarbon fluids, volatile dimethylsiloxanes and mixtures thereof. The main purpose of the oil phase is to provide enhanced esthetic properties, such as emolliency, slip during application over the skin, and an improved perception of dryness, to increase consumer acceptance of the composition.

The oil phase is insoluble in water and therefore is emulsified, preferably with a nonionic emulsifier. Anionic and cationic emulsifiers have the ability to interact with the antiperspirant compound or the borate crosslinker, and thereby reduce composition stability and efficacy. Especially, preferred emulsifiers are nonionic surfactants, or blends thereof, having a hydrophilic-lipophilic balance (HLB) of about 2 to about 18. Particularly preferred emulsifiers are ethoxylated and/or propoxylated fatty ($C_4$ to $C_{22}$) alcohols and mixtures thereof.

The compositions of Examples 6 and 7 further illustrate the antiperspirant deodorant compositions of the present invention.

| Ingredients | Example 6[1)] | Example 7 |
|---|---|---|
| (Phase I) | | |
| Antiperspirant Compound | 21.5 | 20.0 |
| Carrier | 54.0[17)] | 57.5[18)] |
| (Phase II) | | |
| Hydrophilic Polymer | 24.0[19)] | 22.0[20)] |
| Fragrance | 0.5 | 0.5 |

[17)] 30% glycerin and 70% water;
[18)] 17.4% propylene glycol and 82.6% water;
[19)] 12.5% cetyl dimethicone copolyol, available as ABIL ® EM 90 and 87.5% of a blend of cyclomethicone and dimethicone copolymer, available as AMERSIL ® ME-358, both from Goldschmidt Chemical Corp., Hopewell, VA; and
[20)] AMERSIL ® ME-358.

The compositions of Examples 6 and 7 were prepared by adding the ingredients of phase I at room temperature in a suitable vessel, adding the antiperspirant compound last. Separately, the ingredients of phase II were mixed in a second vessel at room temperature. Phase I then was added to phase II, slowly, and with mixing. The admixture initially was very viscous, then set into a gel. The composition of Example 6 was a water-clear gel. The composition of Example 7 was a slightly hazy gel. The compositions of Examples 6 and 7 each exhibited good tactile properties.

Roll-on or gel antiperspirant compositions of the present invention incorporating a hydrophobic compound exhibited consumer-acceptable tack, transparency, viscosity or firmness, and pay-off (ability to deliver the antiperspirant compound) to the skin. The transparency of the antiperspirant compositions was determined spectrophotometrically by measuring % transmittance at 700 nm (nanometers), using water as the standard for 100% transmittance.

A transparent, roll-on or gel antiperspirant compositions of the present invention including emulsified hydrophobic components can be prepared. By a judicious choice of ingredients, the transparent roll-on or gel antiperspirant compositions demonstrate excellent esthetic and functional properties, such as transparency, pay-off, viscosity or firmness and low tack. In addition, the compositions leave no visually-observable white residue on skin or clothing. The compositions exhibited an excellent stability at room temperature.

The antiperspirant compositions of the present invention exhibit unique and superior properties upon topical application to skin. The improved physical and sensory properties include a sufficient viscosity or a firm consistency to effectively deliver the antiperspirant compound to the skin; storage stability; elimination of the shaking requirement to redistribute the antiperspirant compound prior to use; essentially no whitening of the skin and clothing after topical application; and transparency for enhanced consumer acceptance.

It should be understood that the foregoing detailed description is given merely by way of illustration. Obviously, many modifications and variations of the invention as hereinbefore set forth can be made without departing from the spirit and scope thereof and therefore only such limitations should be imposed as are indicated by the appended claims.

What is claimed and desired to be secured by Letters Patent is:

1. A roll-on or gel antiperspirant composition comprising:
   (a) about 1% to about 40% by weight of an antiperspirant compound;
   (b) about 0.005% to about 10% by weight of a hydrophilic polymer selected from the group consisting of a polyethylene glycol, having a weight average molecular weight of at least about 5,000; and
   (c) a carrier comprising water, a water-soluble solvent and mixtures thereof;
   wherein the antiperspirant composition has a pH of about 2 to about 6.

2. The antiperspirant composition of claim 1 further comprising:
   (e) 0% to about 15% by weight of a softening agent having an HLB value of at least about 6, a weight average molecular weight of less than about 10,000, and selected from the group consisting of a polyoxyethylene ether of a fatty ($C_6$–$C_{22}$) alcohol, a polyoxypropylene ether of a fatty ($C_6$–$C_{22}$) alcohol, a dimethicone copolyol, a polypropylene glycol, an ethoxylated alkylphenol, a polyethylene glycol ether of methyl glucose, and mixtures thereof.

3. The antiperspirant composition of claim 1 further comprising 0% to about 10% by weight of a hydrophobic compound selected from the group consisting of an aliphatic hydrocarbon, a fatty ($C_8$–$C_{22}$) alcohol, a fatty alcohol benzoate ester, a siloxane, and mixtures thereof, wherein the hydrophobic compound is emulsified by an emulsifying surfactant.

4. The antiperspirant composition of claim 1 having a viscosity of about 30 to about 200,000 centipoise.

5. The antiperspirant composition of claim 1 wherein the composition is a roll-on having a viscosity of about 100 to about 3000 centipoise.

6. The antiperspirant composition of claim 1 wherein the composition is a gel having a viscosity of about 50,000 to about 200,000 centipoise millimeters.

7. The antiperspirant composition of claim 1 wherein the composition has a % transmittance at 700 nm of at least 50%.

8. The antiperspirant composition of claim 1 wherein the antiperspirant compound is present in an amount of about 5% to about 30% by weight of the composition.

9. The antiperspirant composition of claim 1 wherein the antiperspirant compound is present in an amount of about 10% to about 25% by weight of the composition.

10. The antiperspirant composition of claim 1 wherein the antiperspirant compound is an astringent salt comprising aluminum, zirconium, zinc or a mixture thereof.

11. The antiperspirant composition of claim 1 wherein the antiperspirant compound is selected from the group consisting of aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof.

12. The composition of claim 1 wherein the hydrophilic polymer is present in an amount of about 0.01% to about 5% by weight of the composition.

13. The composition of claim 1 wherein the hydrophilic polymer is present in an amount of about 0.1% to about 3% by weight of the composition.

14. The composition of claim 1 wherein the hydrophilic polymer has a weight average molecular weight of about 5,000 to about 5,000,000.

15. The composition of claim 1 wherein the hydrophilic polymer comprises a polyethylene glycol having a weight average molecular weight of about 15,000 to about 5,000,000.

16. The composition of claim 15 wherein the polyethylene glycol has a molecular weight of about 100,000 to about 4,000,000.

17. The composition of claim 1 having a pH of about 3 to about 5.

18. The composition of claim 1 wherein the carrier is selected from the group consisting of water, ethylene glycol, propylene glycol, butylene glycol, propylene carbonate, dimethyl isosorbide, hexylene glycol, ethanol, n-butyl alcohol, n-propyl alcohol, isopropyl alcohol, and mixtures thereof.

19. The composition of claim 2 wherein the softening agent is selected from the group consisting of methyl gluceth-20, methyl gluceth-10, a $C_{12-15}$ alkyl benzoate, PEG-20 methyl glucose distearate, PEG-20 methyl glucose sesquistearate, PEG-200 castor oil, PEG-6, PEG-8, $C_{11-15}$ pareth-20, nonoxynol-9, octoxynol-10, nonyl nonoxynol-10, ceteth-8, ceteth-12, dodoxynol-12, laureth-15, PEG-20, PEG-3 castor oil, PEG-8 castor oil, PEG-20 castor oil, poloxamer 101, polysorbate 20, PPG-11 stearyl ether, dimethicone copolyol, steareth-20, and mixtures thereof.

20. The antiperspirant composition of claim 3 wherein tile hydrophobic compound is an aliphatic hydrocarbon selected from the group consisting of isohexadecane, 1-decene dimer, a mineral oil, a nonvolatile hydrocarbon fluids, and a hydrocarbon depicted by general structural formula

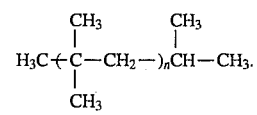

21. The antiperspirant composition of claim 3 wherein the hydrophobic compound is selected from the group consisting of a cyclic volatile siloxane, a linear volatile siloxane, a linear nonvolatile siloxane, a methicone, a phenyltrimethicone, bisphenylhexamethicone, and mixtures thereof.

22. The antiperspirant composition of claim 3 wherein the emulsifying surfactant is a nonionic surfactant having a HLB value of about 2 to about 18.

23. A roll-on or gel antiperspirant composition comprising:
(a) about 5% to about 30% by weight of an aluminum halide, an aluminum hydroxyhalide a zirconyl oxyhalide, a zirconyl hydroxyhalide, an aluminum zirconium glycinate, or a mixture thereof;
(b) about 0.005% to about 5% by weight of a hydrophilic polymer selected from the group consisting of a polyethylene glycol having a weight average molecular weight of about 15,000 to about 4,000,000; and
(c) a carrier selected from the group consisting of water, propylene glycol, ethanol and mixtures thereof.

24. The composition of claim 23 further comprising:
(e) 0% to about 12% by weight of a softening agent selected from the group consisting of methyl gluceth-20, methyl gluceth-10, a $C_{12-15}$ alkyl benzoates, PEG-20 methyl glucose distearate, PEG-20 methyl glucose sesquistearate, PEG-200 castor oil, PEG-6, PEG-8, $C_{11-15}$ pareth-20, nonoxynol-9, octoxynol-10, nonyl nonoxynol-10, ceteth-8, ceteth-12, dodoxynol-12, laureth-15, PEG-20, PEG-3 castor oil, PEG-8 castor oil, PEG-20 castor oil, poloxamer 101, polysorbate 20, PPG-11 stearyl ether, dimethicone copolyol, steareth-20, and mixtures thereof.

25. The composition of claim 23 further comprising 0% to about 10% by weight of a hydrophobic compound selected from the group consisting of a volatile cyclic siloxane, a volatile linear siloxane, a nonvolatile linear siloxane, isohexadecane, 1-decene dimer, a volatile hydrocarbon having the formula

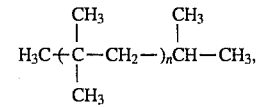

wherein n ranges from 2 to 5, and mixtures thereof.

26. A method of treating or preventing malodors associated with human perspiration comprising topically applying an effective amount of an antiperspirant composition to human skin, said composition comprising:

(a) about 1% to about 40% by weight of an antiperspirant compound;

(b) about 0.005% to about 10% by weight of a hydrophilic polymer selected from the group consisting of a polyethylene glycol having a weight average molecular weight of at least about 5,000; and (c) a carrier comprising water, a water-soluble solvent and mixtures thereof;

wherein the antiperspirant composition has a pH of about 2 to about 6.

27. The method of claim 26 wherein the human skin having the antiperspirant composition applied thereon has no visually-observable white residue.

* * * * *